United States Patent
Ou et al.

(10) Patent No.: US 7,626,688 B2
(45) Date of Patent: Dec. 1, 2009

(54) OPTICAL MEASURING SYSTEM WITH A HIGH-SPEED OPTICAL SENSING DEVICE ENABLING TO SENSE LUMINOUS INTENSITY AND CHROMATICITY

(75) Inventors: Tsung-Hsien Ou, Yuanlin Township, Changhua County (TW); Hsin-Yueh Sung, Jhonghe (TW); Hong-Da Jian, Taishan Township, Taipei County (TW); Chi-Cheng Kuan, Sindian (TW); Wen-Chi Luo, Keelung (TW)

(73) Assignee: Chroma Ate Inc., Taoyuan Hsien (TW)

( * ) Notice: Subject to any disclaimer, the term of this patent is extended or adjusted under 35 U.S.C. 154(b) by 120 days.

(21) Appl. No.: 12/078,018

(22) Filed: Mar. 26, 2008

(65) Prior Publication Data

US 2008/0297771 A1 Dec. 4, 2008

(30) Foreign Application Priority Data

May 29, 2007 (TW) .............................. 96119199 A

(51) Int. Cl.
*G01J 3/50* (2006.01)
*G01N 21/00* (2006.01)

(52) U.S. Cl. .......................... 356/73; 356/402; 356/218; 250/226

(58) Field of Classification Search .................. 356/73, 356/402, 218
See application file for complete search history.

(56) References Cited

U.S. PATENT DOCUMENTS

| 7,369,239 | B2 * | 5/2008 | Nagashima et al. | 356/405 |
| 7,388,665 | B2 * | 6/2008 | Ashdown | 356/419 |
| 2003/0020897 | A1 * | 1/2003 | Griffiths et al. | 356/73 |

* cited by examiner

*Primary Examiner*—F. L Evans
(74) *Attorney, Agent, or Firm*—Birch, Stewart, Kolasch & Birch, LLP

(57) ABSTRACT

A high-speed optical sensing device is provided in the present invention. The high-speed optical sensing device has an optical detector, a lens set, and a beam splitter. The optical detector is utilized for detecting luminous intensity. The lens set is utilized for concentrating light beams toward a color analyzer. The beam splitter is aligned to the illuminating device to be detected and is utilized to separate the light beam generated by the illuminating device to the optical detector and the lens set simultaneously.

27 Claims, 4 Drawing Sheets

OPTICAL MEASURING SYSTEM WITH A HIGH-SPEED OPTICAL SENSING DEVICE ENABLING TO SENSE LUMINOUS INTENSITY AND CHROMATICITY

BACKGROUND OF THE INVENTION (1) Field of the Invention

This invention relates to an optical measuring system, and more particularly relates to the optical measuring system enabling to detect luminous intensity and chromaticity simultaneously.

(2) Description of the Prior Art

In present, various standard optical measuring systems are available for detecting LED chips or LED lamps. However, there has no suitable optical measuring system available for detecting LED light bars. Users have to adapt the optical measuring systems specified for detecting LED chips or LED lamps to detect LED light bars.

The optical measuring systems for detecting LED chips or LED lamps are designed to detect single isolated light source. In contrast, the LED light bar has a plurality of LED chips independently illuminate. Luminous intensity and chromaticity of each LED chip on the light bar should be detected. If the influence from the other LED chips on the light bar cannot be effectively removed, the detection cannot be correct.

FIG. 1 is a schematic view showing a typical optical measuring system detecting luminous intensity and chromaticity by using integrating sphere. As shown, light beams from the LED A to be detected project to an integrating sphere 14 through a tube 12. An optical sensor 16 is assembled on the integrating sphere 14 for detecting luminous intensity with unit Lumen. The integrating sphere 14 is connected to a fiber bundle 18 to transmit illumination to a spectrometry (not shown in this figure) for detecting chromaticity. It is noted that light beams generated by the LED A are uniformly diffuse reflected within the integrating sphere 14. Thus, the optical signals accessed in the optical sensor 16 and the fiber bundle 18 would not be affected by the intensity distribution of the light beams from the LED A. However, the optical measuring system has a poor efficiency about using the illumination of the LED A because only the light beams projecting to the optical sensor 16 and the fiber bundle 18 are collected.

FIG. 2 is a schematic view showing another typical optical measuring system. As shown, the optical measuring system has a lens 22, an aperture mirror 24, an optical receiver 28, and a view finder 26. The aperture mirror 24 is substantially located on a focal plane behind the lens 22. The light beams generated by the LED A are concentrated by the lens 22 to the aperture mirror 24. Part of the light beams arriving the aperture mirror 24 are reflected by the aperture mirror 24 to the view finder 26, and the other light beams penetrate the opening of the aperture mirror 24 and reach the optical receiver 28 behind the aperture mirror 24. The optical receiver 28 has a lens 28a and a light guide 28b. The light guide 28b is located behind the lens 28a. The light beams penetrating the aperture mirror 24 are concentrated by the lens 28a to the inlet of the light guide 28b, passing through the light guide 28, and projected to a spectrometry 29. The view finder 26 has a reflector 26a. The light beams projected to the view finder 26 are reflected by the reflector 26a toward the user's eyes for user to check whether the lens 22 is aligned to the LED A.

The view finder 26 is helpful for aligning the lens 22 to the LED A to be detected. The influence from the other LEDs B, C on the light bar can be reduced thereby. However, the settlement of the view finder 26 may increase the cost, size, and weight of the whole system. In addition, the optical measuring system uses the spectrometry 29 to detect absolute radiation spectrum of the LED A. The luminous intensity and chromaticity of the LED A computed by using absolute radiation spectrum detected usually takes a long calculation time and is not suitable for on-line high-speed measurement.

It is noted that the optical measuring systems provided in FIGS. 1 and 2 are specified for detecting single illuminating device. As the optical measuring systems are used to detect the LED A on the light bar 100, the unwanted influence of the other LED chips B, C on the light bar 100 or background illumination may result in measuring error.

Accordingly, it has become a major issue to reduce the influence of background illumination and to detect luminous intensity and chromaticity of the illuminating device rapidly and correctly.

SUMMARY OF THE INVENTION

It is an object of the present invention to provide an optical measuring system for detecting illuminating devices on the light bar precisely.

It is another object of the present invention to provide an optical measuring system for detecting luminous intensity and chromaticity of the illuminating device simultaneously. It is also an object of the present invention to increase detecting speed and accuracy by effectively using the illumination generated by the illuminating device to be detected.

A high-speed optical sensing device for detecting luminous intensity and chromaticity of an illuminating device is provided in the present invention. The high-speed optical sensing device comprises an optical detector, a lens set, and a beam splitter. Wherein, the optical detector is utilized for detecting the luminous intensity. The lens set is utilized for concentrating light beams from the illuminating device toward a color analyzer. The beam splitter is aligned to the illuminating device to be detected and is utilized to separate the light beam generated by the illuminating device to the optical detector and the lens set simultaneously.

An optical measuring system with the high-speed optical sensing device is also provided in the present invention. Except the above mentioned high-speed optical sensing device, the optical measuring system further has a signal operation device. The signal operation device comprises an optical power meter and a color analyzer. The optical power meter is utilized for accessing a detected signal from the optical detector to calculate the luminous intensity of the illuminating device. The color analyzer is utilized for accessing the light beams concentrated by the lens set to detect chromaticity of the illuminating device.

BRIEF DESCRIPTION OF THE DRAWINGS

The present invention will now be specified with reference to its preferred embodiment illustrated in the drawings, in which.

DESCRIPTION OF THE PREFERRED EMBODIMENT

Figure 3:
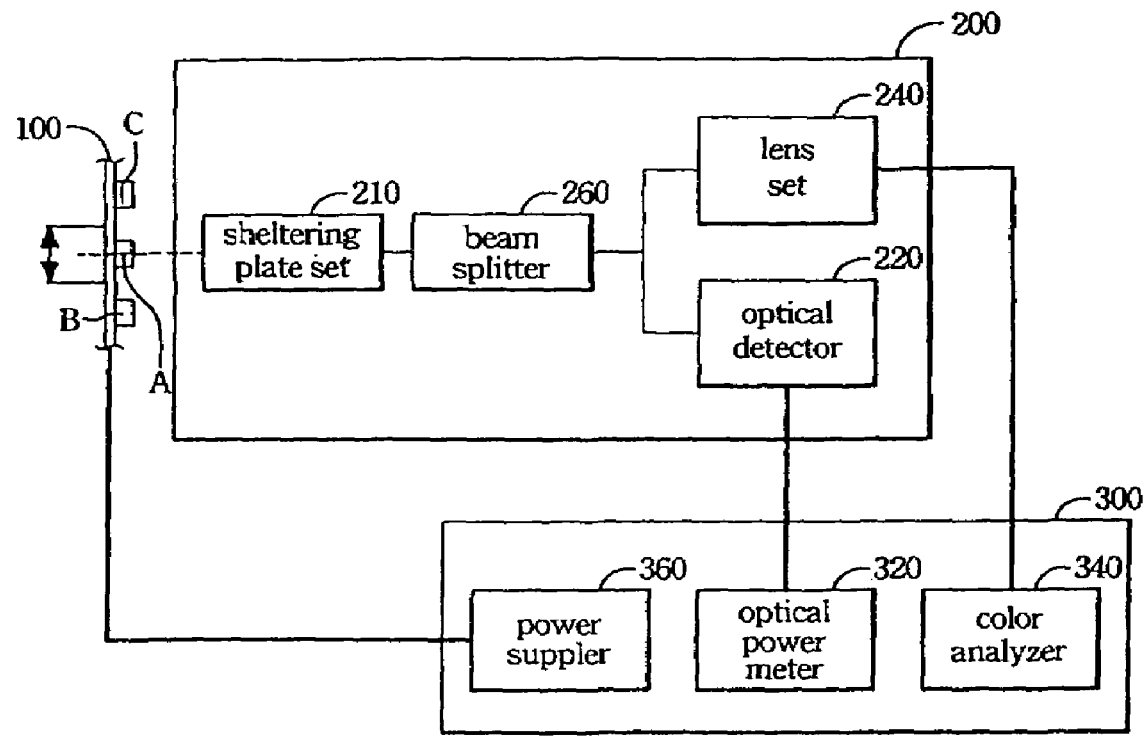
FIG. 3 is a block diagram showing a first preferred embodiment of an optical measuring system in the present invention.

FIG. 3 is a block diagram showing a preferred embodiment of the optical measuring system in the present invention. As shown, the optical measuring system has a high-speed optical sensing device 200 and a signal operation device 300. The high-speed optical sensing device 200 has an optical detector 220, a lens set 240, and a beam splitter 260. The optical detector 220 is utilized for detecting luminous intensity of the illuminating device A to be detected, such as an LED. The lens set 240 is utilized for concentrating light beams from the illuminating device A to a color analyzer (not shown). The beam splitter 260 is aligned to the illuminating device A. Light beams generated by the illuminating device A are separated by the beam splitter 260 into two portions. The two portions of the light beams are projected to the optical detector 220 and the lens set 240 simultaneously.

The signal operation device 300 has an optical power meter 320 and a color analyzer 340. The optical power meter 320 is utilized for accessing detected signals, which may be an electronic signal, from the optical detector 220 to calculate the luminous intensity of the illuminating device A. The color analyzer 340 accesses the optical signal from the lens set 240 to measure chromaticity of the illuminating device A. The color analyzer 340 may be a spectrometry or a three-stimulus color analyzer. In addition, a power supplier 360 can be integrated in the signal operation device 300 to supply electric current to the illumination module 100 such as a light bar.

Figure 4:
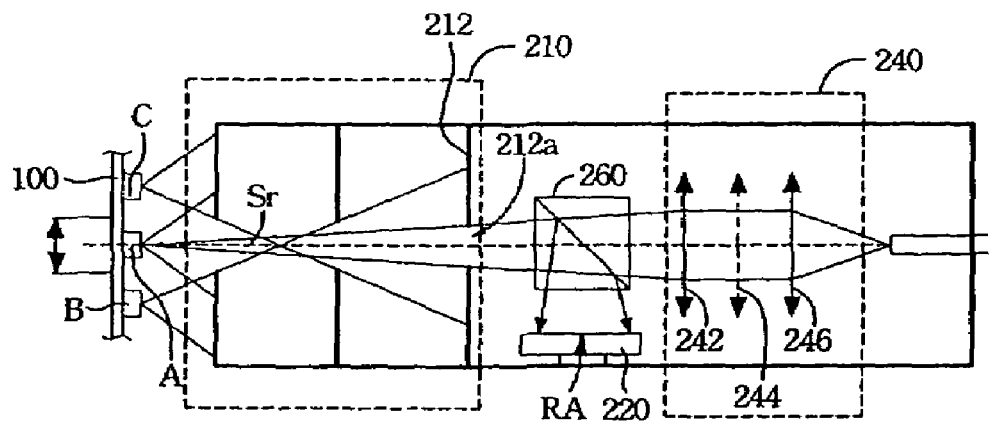
FIG. 4 is a schematic view showing a first preferred embodiment of the optical sensing device of FIG. 3.

FIG. 4 is a schematic view showing a first preferred embodiment of the high-speed optical sensing device 200 in FIG. 3. As shown, the high-speed optical sensing device 200 has a sheltering plate set 210, an optical detector 220, a lens set 240, and a beam splitter 260. The sheltering plate set 210 has at least one sheltering plate 212 located between the beam splitter 260 and the illuminating device A. Three sheltering plates 212 are shown in this figure. Each sheltering plate 212 has an opening 212a aligned to the illuminating device A. The sheltering plate set 210 is utilized for sheltering inclination light beams generated by the other illuminating devices B and C, background illumination, and diffuse illumination reflected by inner walls of the optical sensing device 200, so as to prevent measuring accuracy and repeatability from being affected by such unwanted illumination. It is noted that the usage of sheltering plate set 210 is merely an embodiment and should not be a restriction to the present invention. For example, as another preferred embodiment, a sunshade may be assembled between the beam splitter 260 and the illuminating device A instead.

It is noted that detecting area RA of the optical detector 220 decides a solid angle Sr of the light beams detected by the high-speed optical sensing device 200. As a preferred embodiment, the size of the opening 212a on the sheltering plate 210 should match the solid angle Sr. As a preferred embodiment, the solid angle Sr must satisfy CIE-127 standard about averaged LED intensity to generate standardized measuring data. According to the standard, when the detecting area RA is a 100 cm² circular area, a distance between the illuminating device A and the optical detector 220 should be 316 cm (standard A) or 100 cm (standard B). That is, the solid angle of the light beam to be detected should be 0.001 (standard A) or 0.01 (standard B).

The beam splitter 260 is located behind the sheltering plate set 210 and is utilized for separating the light beams generated by the illuminating device A to the optical detector 220 and the lens set 240 simultaneously. In the present embodiment, a portion of the light beams generated by the illuminating device A penetrates the beam splitter 260 projecting to the lens set 240, and the other portion of the light beams is reflected by the beam splitter 260 to the optical detector 220. The lens set 240 has a first lens 242, an ND filter 244, and a second lens 246. A distance between the first lens 242 and the illuminating device A equals a focal length of the first lens 242. Thus, the light beams from the illuminating device A is transformed into parallel light beams by the first lens 242. The ND filter is located between the first lens 242 and the second lens 246, and it is utilized for adjusting an amount of light projecting to the color analyzer 340 (also referring to FIG. 3) so as to prevent an excess of the detecting range of the color analyzer 340. The second lens 246 is utilized for concentrating the parallel light beams penetrating the ND filter 244 to the color analyzer 340. In the present embodiment, the light beams are concentrated by the second lens 246 to an inlet of a fiber bundle, and then transmitted to the color analyzer 340 through the fiber bundle.

Figure 5:
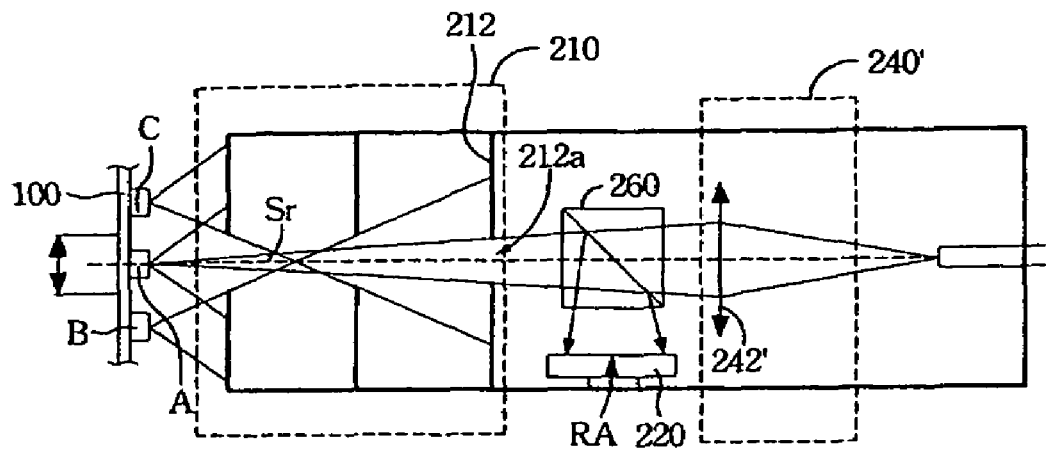
FIG. 5 is a schematic view showing a second preferred embodiment of the optical sensing device in the present invention.

FIG. 5 is a schematic view showing a second preferred embodiment of the high-speed optical sensing device in the present invention. In contrast with the embodiment shown in FIG. 4, the lens set 240' of the present embodiment merely has a first lens 242' for concentrating the light beams generated by the illuminating device A to the color analyzer.

Figure 6:
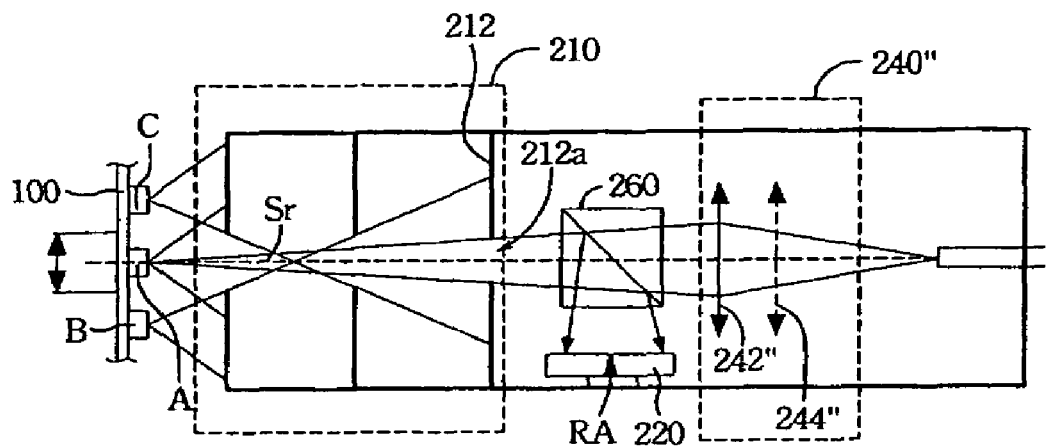
FIG. 6 is a schematic view showing a third preferred embodiment of the optical sensing device in the present invention.

FIG. 6 is a schematic view showing a third preferred embodiment of the high-speed optical sensing device in the present invention. In contrast with the embodiment shown in FIG. 4, the lens set 240" in the present embodiment has a first lens 242" and an ND filter 244". The first lens 242" is utilized for concentrating the light beams generated by the illuminating device A to the color analyzer. The ND filter 244" is located behind the first lens 242" for adjusting an amount of light projecting to the color analyzer.

Figure 7:
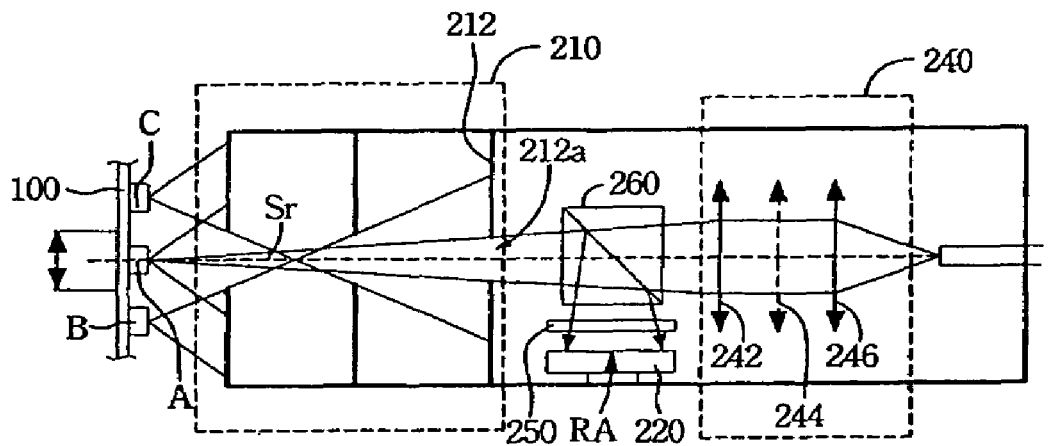
FIG. 7 is a schematic view showing a fourth preferred embodiment of the optical sensing device in the present invention.

FIG. 7 is a schematic view showing a fourth preferred embodiment of the high-speed optical sensing device in the present invention. In contrast with the embodiment shown in FIG. 4, a visual function filter 250 is added between the optical detector 220 and the beam splitter 260 for transforming ordinary luminous information of the illuminating device A into human-vision luminous information.

Figure 1:
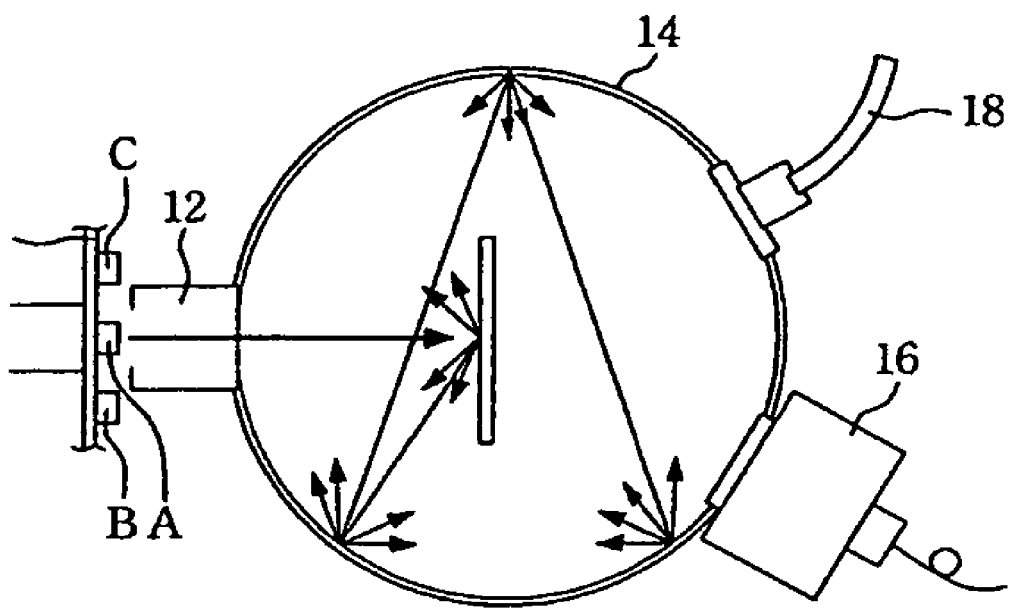
FIG. 1 is a schematic view showing a typical optical measuring system.

The optical measuring system of FIG. 1 has a drawback of lacking efficiency about using illumination from the illuminating device A. In contrast, the light beams generated by the illuminating device A are totally used and separated by the beam splitter 260 into two portions. One is delivered to the color analyzer 340 through the lens set 240, and the other is projected to the optical detector 220. The lens set 240 is capable for increasing luminous intensity of optical signal accessed by the color analyzer 340 to enhance signal-noise ratio thereof. Thus, the optical measuring system in the present invention is capable to use illumination from the illuminating device A efficiently, so as to reduce calculation time needed for the color analyzer 340 to compute chromaticity and enhance high-speed measurement stability.

Figure 2:
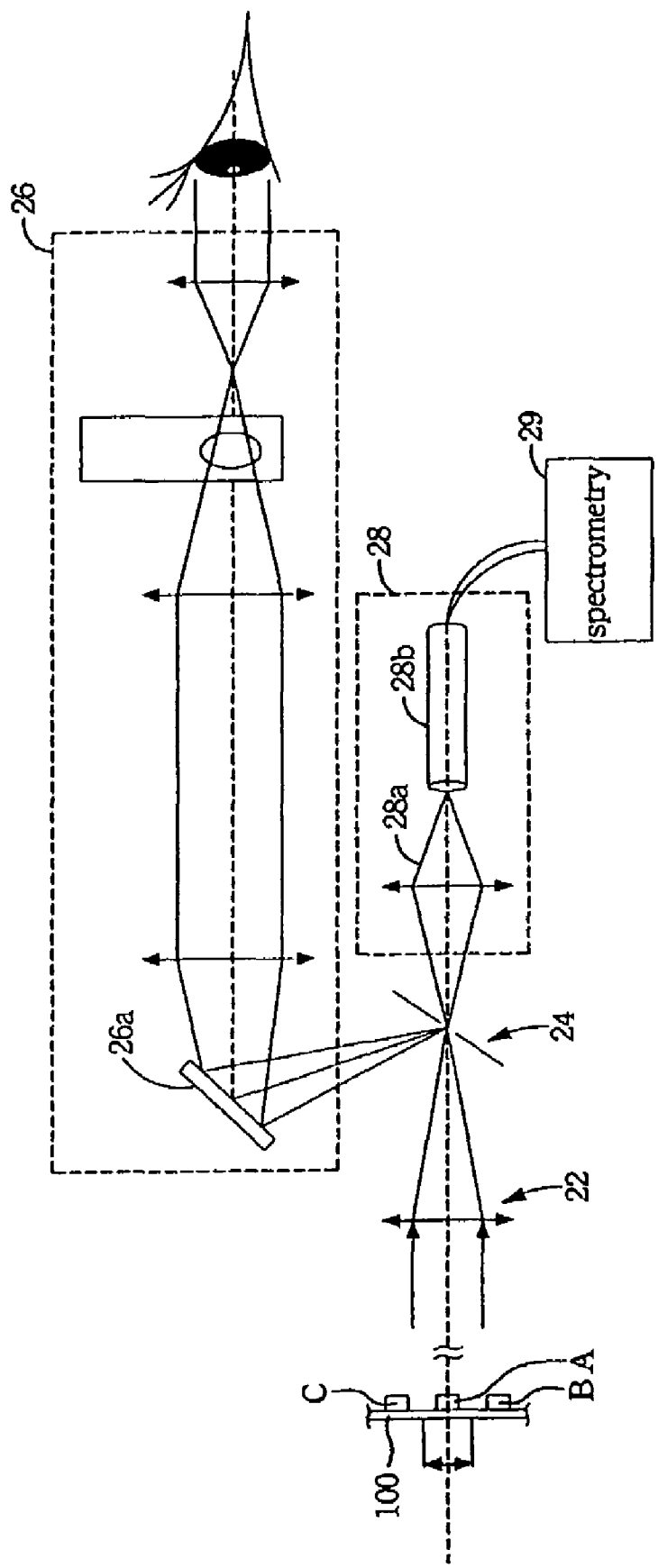
FIG. 2 is a schematic view showing another typical optical measuring system.

The optical measuring system of FIG. 2 calculates luminous intensity and chromaticity by using absolute radiation spectrum accessed by the optical spectrometry. The calculation time is hard to reduce. In contrast, the present invention uses the color analyzer 340 to calculate chromaticity and the optical power meter 320 to compute luminous intensity, respectively. This calculation process is capable to simplify complexity of calculation, reduce calculation time, and fulfills the need of on-line high-speed measurement.

While the preferred embodiments of the present invention have been set forth for the purpose of disclosure, modifications of the disclosed embodiments of the present invention as well as other embodiments thereof may occur to those skilled in the art. Accordingly, the appended claims are intended to cover all embodiments which do not depart from the spirit and scope of the present invention.

What is claimed is:

1. A high-speed optical sensing device for detecting luminous intensity and chromaticity of an illuminating device to be detected, the high-speed optical sensing device comprising:
   an optical detector, for detecting the luminous intensity;
   a lens set, for concentrating light beams from the illuminating device toward a color analyzer; and
   a beam splitter, aligned to the illuminating device for separating light beams generated by the illuminating device to the optical detector and the lens set simultaneously.

2. The high-speed optical sensing device of claim 1, wherein the illuminating device is located on a focal plane in front of the lens set.

3. The high-speed optical sensing device of claim 1, wherein the lens set comprises a first lens and a neutral density (ND) filter, the first lens is utilized for concentrating light beams from the illuminating device to the color analyzer, and the ND filter is utilized for adjust an amount of light accessed by the color analyzer.

4. The high-speed optical sensing device of claim 1, wherein the lens set comprises a first lens and a second lens, the first lens is utilized for transforming light beams from the illuminating device into parallel light beams, and the second lens is utilized for concentrating the parallel light beams to the color analyzer.

5. The high-speed optical sensing device of claim 4, wherein the lens set further comprises a ND filter located between the first lens and the second lens for adjusting an amount of light accessed by the color analyzer.

6. The high-speed optical sensing device of claim 1, wherein a detecting area of the optical detector decides a solid angle of light beams to be detected from the illuminating device.

7. The high-speed optical sensing device of claim 6, wherein the solid angle obeys CIE standard.

8. The high-speed optical sensing device of claim 7, wherein the solid angle substantially equals to 0.001 or 0.01.

9. The high-speed optical sensing device of claim 6, further comprising a sheltering plate, located between the beam splitter and the illuminating device, the sheltering plate has an opening aligned to the illuminating device, and a size of the opening matches the solid angle.

10. The high-speed optical sensing device of claim 1, further comprising a sheltering plate located between the beam splitter and the illuminating device, and the sheltering plate has an opening aligned to the illuminating device.

11. The high-speed optical sensing device of claim 1, further comprising a sunshade located between the beam splitter and the illuminating device for shading environmental light.

12. The high-speed optical sensing device of claim 1, further comprising a visual function filter located between the optical detector and the beam splitter for transforming luminous information of the illuminating device into human-vision luminous information.

13. An optical measuring system comprising:
   a high-speed optical sensing device for detecting luminous intensity and chromaticity of an illuminating device to be detected, the high-speed optical sensing device comprising:
      an optical detector, for detecting the luminous intensity;
      a lens set, for concentrating light beams; and
      a beam splitter, aligned to the illuminating device, and utilized to separate light beams generated by the illuminating device to the optical detector and the lens set simultaneously; and
   an operation device, comprising:
      an optical power meter, accessing detected signals from the optical detector to calculate the luminous intensity of the illuminating device; and
      a color analyzer, accessing the light beams concentrated by the lens set to measure chromaticity of the illuminating device.

14. The optical measuring system of claim 13, wherein the illuminating device is located on a focal plane in front of the lens set.

15. The optical measuring system of claim 13, wherein the lens set comprises a first lens and a neutral density (ND) filter, the first lens is utilized for concentrating light beams from the illuminating device to the color analyzer, and the ND filter is utilized for adjust an amount of light accessed by the color analyzer.

16. The optical measuring system of claim 13, wherein the lens set comprises a first lens and a second lens, the first lens is utilized for transforming light beams from the illuminating device into parallel light beams, and the second lens is utilized for concentrating the parallel light beams to the color analyzer.

17. The optical measuring system of claim 16, wherein the lens set further comprises a ND filter located between the first lens and the second lens for adjusting an amount of light accessed by the color analyzer.

18. The optical measuring system of claim 13, wherein a detecting area of the optical detector decides a solid angle of light beams to be detected from the illuminating device.

19. The optical measuring system of claim 18, wherein the solid angle obeys CIE standard.

20. The optical measuring system of claim 19, wherein the solid angle substantially equals to 0.001 or 0.01.

21. The optical measuring system of claim 18, wherein the high-speed optical sensing device further comprising a sheltering plate, located between the beam splitter and the illuminating device, the sheltering plate has an opening aligned to the illuminating device, and a size of the opening matches the solid angle.

22. The optical measuring system of claim 13, wherein the high-speed optical sensing device further comprising a sheltering plate located between the beam splitter and the illuminating device, and the sheltering plate has an opening aligned to the illuminating device.

23. The optical measuring system of claim 13, wherein the high-speed optical sensing device further comprising a sunshade located between the beam splitter and the illuminating device for shading environmental light.

24. The optical measuring system of claim 13, wherein the high-speed optical sensing device further comprising a visual function filter located between the optical detector and the beam splitter for transforming luminous information of the illuminating device into human-vision luminous information.

25. The optical measuring system of claim 13, wherein the operation device further comprising a power supplier for providing current to the illuminating device.

26. The optical measuring system of claim 13, wherein the color analyzer is a spectrometer.

27. The optical measuring system of claim 13, wherein the color analyzer is a three-stimulus color analyzer.

* * * * *